United States Patent [19]
Barbier et al.

[11] Patent Number: 6,136,969
[45] Date of Patent: Oct. 24, 2000

[54] AZEPANES

[75] Inventors: Pierre Barbier, Rixheim, France; Josef Stadlwieser, Basle, Switzerland; Sven Taylor, Riedisheim, France

[73] Assignee: Hoffmann-La Roche Inc., Nutley, N.J.

[21] Appl. No.: 09/215,611

[22] Filed: Dec. 17, 1998

Related U.S. Application Data

[63] Continuation of application No. 08/831,269, Mar. 31, 1997, Pat. No. 5,907,038, which is a continuation of application No. 08/661,276, Jun. 10, 1996, abandoned.

[30] Foreign Application Priority Data

Jul. 5, 1995 [EP] European Pat. Off. ............ 95110473

[51] Int. Cl.[7] .................................................. C07D 223/08
[52] U.S. Cl. ............................................................ 540/604
[58] Field of Search ............................................. 540/604

[56] References Cited

U.S. PATENT DOCUMENTS

| | | | |
|---|---|---|---|
| 4,254,135 | 3/1981 | Walsh et al. | 424/274 |
| 5,907,038 | 5/1999 | Barbier et al. | 540/604 |

FOREIGN PATENT DOCUMENTS

| | | |
|---|---|---|
| 81670/94 | 12/1994 | Australia . |
| 663393 | 12/1904 | European Pat. Off. . |
| 93/03730 | 3/1993 | WIPO . |
| 94/20062 | 9/1994 | WIPO . |

OTHER PUBLICATIONS

Bioorg. Med. Chem. Lett. 1995, 5(18) pp. 2151–2154.

U. Kikkawa et al. Methods Enzymol. 99, pp. 288–298 (1983).

Buhl et al. J. Invest. Dermatol. 92, pp. 315–320 (1989).

Primary Examiner—Mukund J. Shah
Assistant Examiner—Brenda Coleman
Attorney, Agent, or Firm—George W. Johnston; William H. Epstein

[57] ABSTRACT

Compounds of the formula

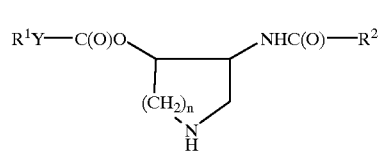

wherein $R^1$ is phenyl or alpha- or beta-naphthyl, which groups can be substituted by hydroxy, lower-alkyl, lower-alkoxy, lower alkoxy-carbonyl, phenoxy, acyloxy, hydroxyphenoxy-sulfonyl, halogen, nitro, amino, acylamino or N-lower-alkyl-acylamino;

$R^2$ is phenyl or phenyl substituted by hydroxy or acyloxy;

Y is a carbon-carbon bond or is vinylene; and n is 1,2 or 3;

and pharmaceutically acceptable acid addition salts thereof are protein kinase inhibitors and can be used for the treatment of disorders mediated by such enzymes, for example, inflammatory diseases.

11 Claims, No Drawings

AZEPANES

This application is a continuation of U.S. application Ser. No. 08/831,269 filed Mar. 31, 1997, now U.S. Pat. No. 5,907,038 which is a continuation of U.S. application Ser. No. 08/661,276 filed Jun. 10, 1996, now abandoned.

BACKGROUND OF THE INVENTION

1. Field of the Invention

The present invention relates to azepanes which inhibit protein kinases.

2. Summary of the Invention

The present invention relates to azepanes and their ring homologs of the formula

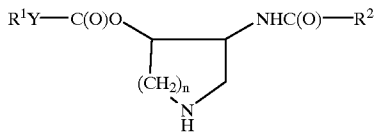

I wherein
- $R^1$ is phenyl or alpha- or beta-naphthyl, which groups can be substituted by hydroxy, lower-alkyl, lower-alkoxy, lower alkoxy-carbonyl, phenoxy, acyloxy, hydroxyphenoxy-sulfonyl, halogen, nitro, amino, acylamino or N-lower-alkyl-acylamino;
- $R^2$ is phenyl or phenyl substituted by hydroxy or acyloxy;
- Y is a carbon-carbon bond or is vinylene; and
- n is 1,2 or 3;

and pharmaceutically acceptable acid addition salts thereof.

The compounds of formula I and their salts can be prepared in accordance with the invention by cleaving off the protecting group Z and, if necessary, hydroxy and amino protecting groups present in $R^{11}$ and $R^{21}$ from a compound of the formula

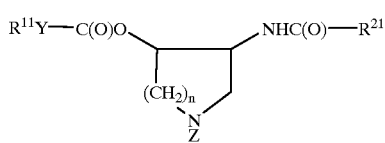

II wherein Z is a protecting group, $R^{11}$ and $R^{21}$ are $R^1$ and $R^2$, respectively, whereby the hydroxy and amino groups contained in $R^1$ and $R^2$ can be present in protected form and $R^1$ and $R^2$, Y and n are as defined above, and, if desired, converting a compound of formula I obtained into a pharmaceutically acceptable salt.

The invention is also concerned with the preparation of the compounds of formula I, pharmaceutical compositions containing a compound of formula I or a pharmaceutically acceptable salt thereof in the manufacture of pharmaceutical compositions for the therapy and prophylaxis of conditions which are mediated by protein kinases.

DETAILED DESCRIPTION OF THE INVENTION

The present invention relates to a compound of the formula

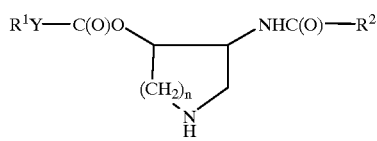

I wherein
- $R^1$ is unsubstituted phenyl, alpha- or beta-naphthyl or phenyl or alpha- or beta-naphthyl substituted by hydroxy, lower-alkyl, lower-alkoxy, lower-alkoxy-carbonyl, phenoxy, acyloxy, hydroxyphenoxy-sulfonyl, halogen, nitro, amino, acylamino or N-lower-alkyl-acylamino;
- $R^2$ is unsubstituted phenyl or phenyl substituted by hydroxy or acyloxy;
- Y is a carbon-carbon bond or vinylene; and
- n is 1, 2 or 3;

and pharmaceutically acceptable acid addition salts thereof.

The term "lower" used here denotes groups with 1–6, preferably 1–4, C atoms. Alkyl and alkoxy groups can be straight-chain or branched, such as methyl, ethyl, propyl, isopropyl, n-butyl, sec.- and tert.-butyl, pentyl and hexyl and, respectively, methoxy, ethoxy, propoxy, isopropoxy, n-butoxy, sec. and tert.- butoxy, pentyloxy and hexyloxy. Acyl groups can be derived from aliphatic, araliphatic or aromatic carboxylic acids, such as saturated and unsaturated aliphatic carboxylic acids, the hydrocarbon residues of which can be straight-chain or branched, particularly lower alkanoic acids, or benzoic acid or benzoic acid substituted by one to three groups selected from hydroxy, lower alkoxy, halogen or nitro. Halogen denotes fluoro, chloro, bromo and iodo.

Preferably $R^1$ is phenyl substituted by phenyl, di-lower alkoxyphenyl, phenoxy, amino, hydroxy, lower alkoxy, lower alkoxy-carbonyl, nitro, halogen, hydroxy-substituted benzoylamino, hydroxy-substituted benzoyl-lower alkylamino, nitrobenzoyloxy and hydroxy-substituted phenoxysulfonyl; and alpha- and beta-naphthyl; and hydroxy- and/or lower alkoxy substituted alpha- and beta-naphthyl.

Preferably $R^2$ is hydroxyphenyl, hydroxy-benzoyloxy-phenyl, di-lower alkyl-benzoyloxy-phenyl, and halogen-benzoyloxy-phenyl, n is preferably 3.

A preferred group of compounds of formula I are those wherein Y is a carbon-carbon bond. Particularly preferred are compounds of formula I wherein $R^1$ is hydroxyphenyl, benzoyloxyphenyl or p-nitrobenzoyloxyphenyl; $R^2$ is phenyl substituted by hydroxy- or hydroxy or halogen-substituted benzoyloxy.

The compounds of formula I and their salts can be prepared in accordance with the invention by cleaving off the protecting group Z and, if necessary, hydroxy and amino protecting groups present in $R^{11}$ and $R^{21}$ from a compound of the formula

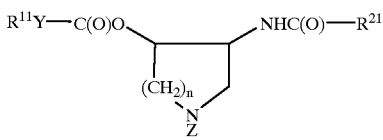

wherein
- Y is a carbon-carbon bond or vinylene;
- Z is a protecting group;
- n is 1, 2 or 3;
- $R^{11}$ is unsubstituted phenyl, alpha- or beta naphthyl or phenyl. alpha- or beta-naphthyl substituted by hydroxy, lower-alkyl, lower-alkoxy, loweralkoxy-carbonyl, phenoxy, acyloxy, hydroxyphenoxy-sulfonyl, halogen, nitro, amino, acylamino or N-lower-alkyl-acylamino whereby the hydroxy and amino groups present are unprotected or protected; and
- $R^{21}$ is phenyl or phenyl substituted by hydroxy or acyloxy whereby the hydroxy and amino groups present are unprotected or protected.

Examples of protecting groups Z and of amino protecting groups present in the substituents $R^{11}$ and $R^{21}$ are groups which are known for the protection of amino groups, such as tert.-butoxycarbonyl. Methoxymethyl, benzyl and silyl ether groups such as tert.-butyl-dimethyl-silanyl are examples of hydroxy protecting groups.

The cleavage of these protecting groups can be carried out in a known manner, such as by treatment with acids, for example, mineral acids, such as HCl, in an inert organic solvent, for example, an ether such as dimethoxyethane or an alcohol such as isopropanol or mixtures of such solvents, or by hydrogenolysis in the case of benzyl ether groups. The acid cleavage of the protecting groups is conveniently effected at low temperatures, preferably at temperatures below room temperature, especially at about 0° C. Hydrogenolytic removal of a benzyl ether group is conveniently carried out using a noble metal catalyst, such as Pd/C at room temperature.

The compounds of formula I form salts in which they can be converted in a known manner. Examples of pharmaceutically acceptable salts of the compounds of formula I are acid addition salts of mineral acids or organic acids, such as hydrochloric acid or trifluoro acetic acid.

The compounds of formula II that are used to prepare the compounds of formula I are novel and also form part of the invention. They can be obtained as described in the Examples given below or in analogy thereto.

The compounds of formula I and their pharmaceutically usable salts are protein kinase inhibitors; they inhibit cellular processes such as cell proliferation and cell secretion and can be used for the control or prevention of illnesses which are mediated by protein kinases, for example, of inflammatory diseases, such as, arthritis. The compounds of formula I may also be useful in treating other disorders mediated by protein kinase, such as immune diseases, psoriasis, contact dermatitis, in connection with organ transplants, as well as, in oncology. They inhibit cell infections with HIV (human immunodeficiency virus) or Epstein-Barr virus and are therefore suitable for the treatment of AIDS and infectious mononucleosis. Furthermore, the compounds in accordance with the invention inhibit smooth muscle contraction and can therefore be used in cardiovascular and bronchopulmonary illnesses. Further, they are of value in asthma therapy. The compounds in accordance with the invention also inhibit blood platelet aggragation and can be used for the control or prevention of thromboses. Furthermore, they inhibit the liberation of mediators of activated neutrophils and can therefore be used in the control of ischemic damage, for example, in the heart or brain. Further, they inhibit neurotoxicity caused by increased glucose level and are therefore of value in the treatment of diabetic complications. Finally, the compounds in accordance with the invention stimulate hair growth and can therefore be used for the prevention or suppression of hair loss.

Protein kinases play an important role as signal transmitters in many cell functions. In addition to tyrosine kinases, serine/threonine kinases such as protein kinase C (PKC) and cyclic AMP-dependent protein kinase (PKA) are key enzymes in the signal transmission chain from the cell membrane to the cell nucleus.

The compounds in accordance with the invention inhibit serine/protein kinases such as PKC and PKA not only as the isolated enzyme but also in cells. They therefore inhibit important cell functions as mentioned above, especially the activation and proliferation of T-lymphocytes and the proliferation of keratinocytes.

Inhibitors of T-cell activation can be used as immunosuppressives for use in illnesses such as rheumatoid arthritis, psoriasis and other inflammatory skin disorders (atopic eczema, contact eczema), in autoimmune diseases, transplants and immunomediated alopecia.

Inhibitors of keratinocyte proliferation are of value for use in skin diseases having a hyperproliferative component in the epidermis, especially psoriasis. Inhibitors of cell proliferation can be used in oncology.

The aforementioned activities can be observed using the test procedures described hereinafter:

A: Inhibition of Protein Kinase C (PKC) (Isolated Enzyme)

Protein kinase C (PKC) activity is determined by measuring the transfer of $^{32}$P-labelled phosphate from $^{32}$P-g-ATP (10 mM) to histone H1 (200 mg/ml) as the substrate. Partially purified PKC from swine brain is used as the enzyme source [DEAE chromatography according to the method of U. Kikkawa et al. (Methods Enzymol. 99, 288, 1983)]. Activation of the PKC is effected by phospholipid vesicle prepared by ultrasound treatment of a mixture of 0.05 ml of phosphatidylserine (10 mg/ml) and 0.005 ml of diolein (10 mg/ml) in 5 ml of Tris-HCl buffer (20 mM, pH 7.4). The test substances are used in dimethyl sulphoxide (DMSO)/buffer in the concentration range 0.001–100 mM. The test is started by the addition of enzyme; after incubation at 32° C. for 2 minutes the reaction is stopped by the addition of 20% trichloroacetic acid (with 1% SDS and 1% sodium pyrophosphate). The precipitated radioactive histone protein is separated from excess ATP by filtration over nitrocellulose membranes and the radioactivity on the filter is measured in a scintillation counter. The inhibitory activity of the test substance is given as the micromolar concentration which is required to reduce the PKC activity by 50% ($IC_{50}$ [mM]).

B: Inhibition of cAMP-Dependent Protein Kinase (PKA)

PKA activity is determined by measuring the transfer of $^{32}$P-labelled phosphate from $^{32}$P-g-ATP (10 mM) to histone H1 (333 mg/ml) as the substrate. Partially purified PKA from swine brain is used as the enzyme source [DEAE chromatography according to the method of U. Kikkawa et al. (Methods Enzymol. 99, 288, 1983)]. Activation of the PKA is effected by cyclic AMP (2 mM) in Tris-HCl buffer (20 mM, pH 7.4). The test substances are used in dimethyl sulfoxide (DMSO)/buffer in the concentration range 0.001–100 mM. The test is started by the addition of enzyme; after incubation at 32° C. for 2 minutes the reaction is stopped by the addition of 20% trichloroacetic acid (with 1% SDS and 1% sodium pyrophosphate). The precipitated radioactive histone protein is separated from excess ATP by filtration over nitrocellulose membranes and the radioactivity on the filter is measured in a scintillation counter. The inhibitory activity of the test substance is given as the micromolar concentration which is required to reduce the PKA activity by 50% ($IC_{50}$ [mM]).

C: Cell Proliferation in Cultured Mouse Hair Follicles

Mouse whisker follicles were isolated and cultured according to the method described by Buhl et al., J. Invest. Dermatol. 92, 315–320 (1989). Whisker pads were removed from 4-day-old CD-1 mice and vibrissae were carefully separated from the surrounding tissue with forceps under a dissecting microscope. Four hair follicles were incubated at 37° C. in 2 $cm^2$ wells in 1 ml of M199 medium containing 20% fetal bovine serum. in the presence or absence of test compound at varying concentrations. Each treatment group consisted of four wells. After 1 day of culture. $^3$H-thymidine was added to the wells to a final concentration of 5 $\mu$Ci/ml and the follicles were incubated for a further three days. The follicles were then washed with phosphate-buffered saline and incorporated radioactivity was solubilized by addition of 0.5 ml of 1.0M NaOH and incubation for 18 h at 37° C. An aliquot of the alkali extracted was taken for measurement of radioactivity and results were expressed as dpm/follicle.

Calculation of Maximal Stimulation and $ED_{50}$ Values

The hair follicle $^3$H-thymidine incorporation values (dpm/follicle), obtained as described above, were then expressed as a percentage of control levels as follows:

% control DNA synthesis for test compound=((treatment dpm/follicle)/(control dpm/follicle))×100

The dose-response relationship for each compound was then used to determine: 1) the maximal stimulation of DNA synthesis obtained for that compound, expressed as a percentage of control levels, and 2) the $ED_{50}$ value, or the concentration ($\mu$M) of compound that gave rise to 50% of the maximal stimulation of DNA synthesis.

The results obtained with typical compounds of formula I in these test procedures are compiled in the following Table I and II:

TABLE I

| Compound of Example | Test Procedure* | |
| --- | --- | --- |
| | A | B |
| I/15 | 8.8 | 0.070 |
| I/19 | 24 | 0.041 |
| I/25 | 26 | 1.9 |
| II/1 | 30 | 0.038 |
| III/1 | 10 | 0.026 |

*the test data indicate the respective $IC_{50}$ [mM]

TABLE II

| | Mouse Hair Follicle DNA Synthesis | |
| --- | --- | --- |
| Compound of Example | Maximal Stimulation (% control) | $EC_{50}$ ($\mu$M) |
| III/1 | 534 ± 52 | 5 |
| II/1 | 468 ± 26 | 10 |

TABLE II-continued

| | Mouse Hair Follicle DNA Synthesis | |
| --- | --- | --- |
| Compound of Example | Maximal Stimulation (% control) | $EC_{50}$ ($\mu$M) |
| I/19 | 371 ± 50 | 30 |
| I/28 | 349 ± 25 | 40 |

The compounds of formula I and their salts can be used as medicaments, for example, in the form of pharmaceutical preparations.

The preparations can be administered enterally, parenterally or topically. Preparations in the form of tablets, capsules, dragees, syrups, suspensions, solutions and suppositories are suitable for example, for enteral administration. Preparations in the form of infusion or injection solutions are suitable for parenteral administration.

The dosages in which the preparations are administered can vary according to the mode of use and route of use and on the requirements of the patient.

In the case of the oral administration of the compounds in accordance with the invention, dosages of about 0.1–100 mg/kg, preferably 0.5–50 mg/kg, per day come into consideration for adults.

The preparations can be administered in one or several dosages. Capsules containing about 5–500 mg of active ingredient represent a preferred dosage form.

The preparations can contain inert as well as pharmacodynamically active additives. Tablets or granulates, for example, can contain a series of binders, fillers, carrier substances or diluents. Liquid preparations can be present, for example, in the form of a sterile water-miscible solution. Capsules can contain, in addition to the active ingredient, a filler or thickener. Furthermore, flavor-improving additives as well as substances usually used as preservatives, stabilizers, water-retainers and emulsifiers as well as salts for varying the osmostic pressure, buffers and other additives can also be present.

The previously mentioned carrier substances and diluents can be organic or inorganic substances, for example, water, gelatin, lactose, starch, magnesium stearate, talc, gum arabic, polyalkylene glycols and the like. It is a prerequisite that all adjuvants used in the manufacture of the preparations are non-toxic.

For topical use, the active ingredients are conveniently used in the form of ointments, tinctures, creams, solutions, lotions, sprays, suspensions and the like. Ointments and creams as well as solutions are preferred. These preparations destined for topical use can be manufactured by admixing the process products as active ingredients with non-toxic, inert, solid or liquid carriers which are suitable for topical treatment and which are conventional in such preparations.

For topical use there are suitable conveniently about 0.1–5%, preferably 0.3–3%, solutions as well as about 0.1–5%, preferably about 0.3–2%, ointments and creams.

If desired, an antioxidant, for example, tocopherol, N-methyl-g-tocopheramine, as well as, t-butyl-hydroxyanisole or t-butyl-hydroxytoluene, can be admixed with the preparations.

The following Examples illustrate the invention further.

EXAMPLE I 1) 56 mg (3R,4R)-3-[4-(4-Fluoro-benzoyloxy)-benzoylamino]-4-(4-hydroxy-benzoyloxy)-azepane-1- carboxylic acid tert-butyl ester was dissolved in 2 ml dimethoxyethane and 2 ml isopropanol (i-Pr-OH); after cooling to 0° C. the solution was slowly saturated with HCl-gas and stored in a refrigerator for 24 h. The solvent was completely removed in vacuo; the product was triturated with diethylether; the resulting suspension was stirred for several hours. The solvent was decanted and stirring was continued overnight after addition of another portion of fresh solvent. The product was filtered, washed with several portions of diethylether and dried in vacuo (0.1 mbar) at 50° C. 40 mg (85% yield) 4-Hydroxy-benzoic acid (3R,4R)-3-[4-(4-fluoro-benzoyloxy)-benzoylamino]-azepan-4-yl ester hydrochloride (1:1) was obtained as a yellow powder MS: m/e=493 (M+H)$^+$ IR (KBr): 3415, 3269, 1741, 1703, 1641, 1605, 1541, 1507 cm$^{-1}$ In analogy there were obtained 2) Biphenyl-4-carboxylic acid (3R,4R)-3-(4-hydroxy-benzoylamino)-azepan-4-yl ester hydrochloride (1:1) from (3R,4R)-4-(Biphenyl-4-ylcarbonyloxy)-3-(4-hydroxy-benzoylamino)-azepane-1-carboxylic acid tert-butyl ester

MS: 431 (M+H)$^+$

IR: 3381, 3249, 2801, 2539, 1706, 1651, 1607, 1594, 1503 cm$^{-1}$

3) Naphthalene-2-carboxylic acid (3R,4R)-3-(4-hydroxy-benzoylamino)-azepan-4-yl ester hydrochloride (1:1) from (3R,4R)-3-(4-Hydroxy-benzoylamino)-4-(naphthalen-2-yl-2-carbonyloxy)-azepane-1-carboxylic acid tert-butyl ester

MS: 405 (M+H)$^+$

IR: 3402, 3265, 3062, 1707, 1854, 1630, 1607, 1535 cm$^{-1}$

4) Naphthalene-1-carboxylic acid (3R,4R)-3-(4-hydroxy-benzoylamino)-azepan-4-yl ester hydrochloride (1:1) from (3R,4R)-3-(4-Hydroxy-benzoylamino)-4-(naphthalen-1-ylcarbonyloxy)-[4-(2-hydroxy-phenoxysulfonyl)-benzoyloxyl-azepane-1-carboxylic acid tert-butyl ester

MS: 404.9 (M+H)$^+$

IR: 3392, 3241, 2801, 2544, 1713, 1635, 1608, 1540, 1506 cm$^{-1}$ 5) 2-Phenoxy-benzoic acid (3R,4R)-3-(4-hydroxy-benzoylamino)-azepan-4-yl ester hydrochloride (1:1) from (3R,4R)-3-(4-Hydroxy-benzoylamino)-4-(2-phenoxy-benzoyloxy)-azepane-1-carboxylic acid tert-butyl ester

MS: 447 (M+H)$^+$

IR: 3404, 3254, 2795, 2554, 1720, 1637, 1607, 1540, 1506, 1482 cm$^{-1}$ 6) 4-Amino-benzoic acid (3R,4R)-3-(4-hydroxy-benzoylamino)-azepan-4-yl ester trifluoroacetate (1:1) from (3R,4R)-4-(4 -tert-Butoxycarbonylamino-benzoyloxy)-3-(4-hydroxy-benzoylamino)-azepane-1-carboxylic acid tert-butyl ester

MS: 370 (M+H)$^+$

IR: 3404, 2626, 1678, 1607, 1508, 1202, 1176, 845, 723 cm$^{-1}$ 7) 3-Phenoxy-benzoic acid (3R,4R)-3-(4-hydroxy-benzoylamino)-azepan-4-yl ester trifluoroacetate (1:1) from (3R,4R)-3-(4-Hydroxy-benzoylamino)-4-(3-phenoxy-benzoyloxy)-azepane-1-carboxylic acid tert-butyl ester

MS: 447 (M+H)$^+$

IR: 3387, 3167, 1722, 1677, 1634, 1607, 1583, 1544, 1509, 1486, 1441 cm$^{-1}$

8) Biphenyl-2-carboxylic acid (3R,4R)-3-(4-hydroxy-benzoylamino)-azepan-4-yl ester trifluoroacetate (1:1) from (3R,4R)-4-(Biphenyl-2-ylcarbonyloxy-2-carbonyloxy)-3-(4-hydroxy-benzoylamino)-azepane-1-carboxylic acid tert-butyl ester

MS: 431 (M+H)$^+$

IR: 3375, 3061, 3027, 2602, 1676, 1638, 1608, 1543, 1507, 1449 cm$^{-1}$ 9) 3-Methoxy-phthalic acid (3R,4R)-1-[3-(4-hydroxy-benzoylamino)-azepan-4-yl]ester 2-methyl ester trifluoroacetate (1:1) from 3-Methoxy-phthalic acid (3R,4R)-1-[1-tert-butoxycarbonyl-3-(4-hydroxy-benzoylamino)-azepan-4-yl] ester 2-methyl ester

MS: 443 (M+H)$^+$

IR: 3405, 3017, 2954, 2848, 1724, 1677, 1638, 1610, 1544 cm$^{-1}$ 10) 3,5-Dimethoxy-naphthalene-2-carboxylic acid (3R,4R)-3-(4-hydroxy-benzoylamino)-azepan-4-yl ester trifluoroacetate (1:1) from (3R,4R)-4-(3,5-Dimethoxy-naphthalen-2-ylcarbonyloxy-)-3-(4-hydroxy-benzoylamino)-azepane-1-carboxylic acid tert-butyl ester

MS: 465 (M+H)$^+$

IR: 3395, 3163, 2837, 1677, 1632, 1605, 1542, 1505, 1469 cm$^{-1}$ 11) 3,7-Dimethoxy-naphthalene-2-carboxylic acid (3R,4R)-3-(4-hydroxy-benzoylamino)-azepan-4-yl ester trifluoroacetate (1:1) from (3R,4R)-4-(3,7-Dimethoxy-naphthalen-2-ylcarbonyloxy)-3-(4-hydroxy-benzoylamino)-azepane-1-carboxylic acid tert-butyl ester

MS: 465 (M+H)$^+$

IR: 3394, 3065, 3009, 1780, 1677, 1636, 1607, 1543, 1507 cm$^{-1}$ 12) 2,5-Dichloro-3-nitro-benzoic acid (3R,4R)-3-(4-hydroxy-benzoylamino)-azepan-4-yl ester trifluoroacetate (1:1 from (3R,4R)-4-(2,5-Dichloro-3-nitro-benzoyloxy)-3-(4-hydroxy-benzoylamino)-azepane-1-carboxylic acid tert-butyl ester

MS: 468 (M+H)$^+$

IR: 3419, 2608, 1738, 1676, 1637, 1607, 1545, 1507, 1440 cm$^{-1}$ 13) 3-(4-Hydroxy-phenyl)-acrylic acid (3R,4R)-3-(4-hydroxy-benzoylamino)-azepan-4-yl ester trifluoroacetate (1:1) from (E)-(3R,4R)-3-(4-Hydroxy-benzoylamino)-4-[3-(4-hydroxy-phenyl)-acryloyloxy]-azepane-1-carboxylic acid tert-butyl ester

MS: 397 (M+H)$^+$

IR: 3385, 2811, 1678, 1633, 1605, 1511, 1202, 1169, 980, 832, 722 cm$^{-1}$ 14) 3',4'-Dimethoxy-biphenyl-4-carboxylic acid (3R,4R)-3-(4-hydroxy-benzoylamino)-azepan-4-yl ester trifluoroacetate (1:1) from (3R,4R)-4-(3',4'-Dimethoxy-biphenyl-4-ylcarbonyloxy)-3-(4-hydroxy-benzoylamino)-azepane-1-carboxylic acid tert-butyl ester

MS: 675 (M+H)$^+$

IR: 3367, 3189, 3006, 2944, 2872, 1784, 1676, 1637, 1607, 1526, 1503 cm$^{-1}$ 15) 3,4-Dihydroxy-benzoic acid (3R,4R)-3-(4-hydroxy-benzoylamino)-azepan-4-yl ester trifluoroacetate (1:1) from (3R,4R)-4-(3,4-Dihydroxy-benzoyloxy)-3-(4-hydroxy-benzoylamino)-azepane-1-carboxylic acid tert-butyl ester

MS: 387 (M+H)$^+$

IR: 3395, 2860, 1678, 1608, 1508, 1294, 1200, 1116, 847, 764, 721 cm$^{-1}$ 16) 2,3-Dihydroxy-benzoic acid (3R,4R)-3-(4-hydroxy-benzoylamino)-azepan-4-yl ester trifluoroacetate (1:1) from (3R,4R)-4-(2,3-Dihydroxy-benzoyloxy)-3-(4-hydroxy-benzoylamino)-azepane-1-carboxylic acid tert-butyl ester

MS: 387 (M+H)$^+$ 17) 7-Hydroxy-3-methoxy-naphthalene-2-carboxylic acid (3R,4R)-3-(4-hydroxy-benzoylamino)-azepan-4-yl ester trifluoroacetate (1:1) from (3R,4R)-3-(4-Hydroxy-benzoylamino)-4-(7-hydroxy-3-methoxy-naphthalenne-2-ylcarbonyloxy)-azepane-1-carboxylic acid tert-butyl ester

MS: 451 (M+H)$^+$

IR: 3386, 3059, 2969, 1785, 1677, 1636, 1608, 1543, 1507 cm$^{-1}$ 18) 2,4-Dihydroxy-benzoic acid (3R,4R)-3-(4-hydroxy-benzoylamino)-azepan-4-yl ester trifluoroacetate (1:1) from (3R,4R)-4-(2,4-Dihydroxy-benzoyloxy)-3-(4-hydroxy-benzoylamino)-azepane-1-carboxylic acid tert-butyl ester

MS: 387 (M+H)$^+$

IR: 3388, 2871, 1781, 1670, 1626, 1507, 1267, 1204, 1177, 1143, 874, 848, 774, 699 cm$^{-1}$ 19) 5-Hydroxy-3-methoxy-naphthalene-2-carboxylic acid (3R,4R)-3-(4-hydroxy-benzoylamino)-azepan-4-yl ester trifluoroacetate (1:1) from (3R,4R)-3-(4-Hydroxy-benzoylamino)-4-(5-hydroxy-3-methoxy-naphthalene-2-ylcarbonyloxy)-azepane-1-carboxylic acid tert-butyl ester

MS: 451 (M+H)$^+$

IR: 3392, 3099. 1676, 1632, 1606, 1543, 1508, 1454 cm$^{-1}$ 20) 3-Hydroxy-5-methoxy-naphthalene-2-carboxylic acid (3R,4R)-3-(4-hydroxy-benzoylamino)-azepan-4-yl ester trifluoroacetate (1:1) from (3R,4R)-3-(4-Hydroxy-benzoylamino)-4-(3-hydroxy-5-methoxy-naphthalene-2-ylcarbonyloxy)-azepane-1-carboxylic acid tert-butyl ester

MS: 451 (M+H)$^+$

IR: 3384, 3288, 2598, 1779, 1680, 1635, 1607, 1542, 1511 cm$^{-1}$ 21) 3-Hydroxy-7-methoxy-naphthalene-2-carboxylic acid (3R,4R)-3-(4-hydroxy-benzoylamino)-azepan-4-yl ester trifluoroacetate (1:1) from (3R,4R)-3-(4-Hydroxy-benzoylamino)-4-(3-hydroxy-7-methoxy-naphthalene-2-ylcarbonyloxy)-azepane-1-carboxylic acid tert-butyl ester

MS: 451 (M+H)$^+$

IR: 3411, 2615, 2594, 1679, 1636, 1608, 1542, 1510, 1470, 1440 cm$^{-1}$ 22) 5-Fluoro-2-hydroxy-benzoic acid (3R,4R)-3-(4-hydroxy-benzoylamino)-azepan-4-yl ester trifluoroacetate (1:1) from (3R,4R)-4-(5-Fluoro-2-hydroxy-benzoyloxy)-3-(4-hydroxy-benzoylamino)-azepane-1-carboxylic acid tert-butyl ester

MS: 389 (M+H)$^+$

IR: 3282, 2852, 1679, 1633, 1607, 1486, 1201, 1070, 832, 784, 723 cm$^{-1}$ 23) 4-Hydroxy-3,5-dimethoxy-benzoic acid (3R,4R)-3-(4-hydroxy-benzoylamino)-azepan-4-yl ester trifluoroacetate (1:1) from (3R,4R )-3-(4-Hydroxy-benzoylamino)-4-(4-hydroxy-3,5-dimethoxy-benzoylox)-azepane-1-carboxylic acid tert-butyl ester

MS: 431 (M+H)$^+$

IR: 3393, 2968, 1678, 1609, 1510, 1338, 1279, 1207, 1181, 1114, 849, 766, 722 cm$^{-1}$ 24) 4-(2-Hydroxy-benzoylamino)-benzoic acid (3R,4R)-3-(4-hydroxy-benzoylamino)-azepan-4-yl ester trifluoroacetate (1:1) from (3R,4R)-3-(4-Hydroxy-benzoylamino)-4-[4-(2-hydroxy-benzoylamino)-benzoyloxy]-azepane-1-carboxylic acid tert-butyl ester

MS: 490 (M+H)$^+$

IR: 3318, 3191, 3065, 2976, 2868, 2591, 1676, 1596, 1535, 1508 cm$^{-1}$ 25) 4-[(2-Hydroxy-benzoyl)-methyl-amino]-benzoic acid (3R,4R)-3-(4-hydroxy-benzoylamino)-azepan-4-yl ester trifluoroacetate (1:1) from (3R,4R)-3-(4-Hydroxy-benzoylamino)-4-{4-[(2-hydroxy-benzoyl)-methyl-amino]-benzoyloxy}-azepane-1-carboxylic acid tert-butyl ester

MS: 504 (M+H)$^+$

IR: 3349, 3267, 2601, 1676, 1633, 1605, 1544, 1508, 1453 cm$^{-1}$ 26) 4-[(2,6-Dihydroxy-benzoyl)-methyl-amino]-benzoic acid (3R,4R)-3-(4-hydroxy-benzoylamino)-azepan-4-yl ester trifluoroacetate (1:1) from (3R,4R)-4-{4-[(2,6-Dihydroxy-benzoyl)-methyl-amino]-benzoyloxy}-3-(4-hydroxy-benzoylamino)-azepane-1-carboxylic acid tert-butyl ester

MS: 520 (M+H)$^+$

IR: 3392, 3118, 2874, 1676, 1605, 1544, 1508, 1467, 1439 cm$^{-1}$ 27) 2-Hydroxy-benzoic acid (3R,4R)-3-(4-hydroxy-benzoylamino)-azepan-4-yl ester trifluoroacetate (1:1) from (3R,4R)-3-(4-Hydroxy-benzoylamino)- 4-(2-hydroxy-benzoyloxy)-azepane-1-carboxylic acid tert-butyl ester

MS: 371 (M+H)$^+$

IR: 3368, 2967, 1676, 1610, 1507, 1203, 1137, 847, 759, 722 cm$^{-1}$ 28) 4-(2-Hydroxy-phenoxysulfonyl)-benzoic acid (3R,4R)-3-(4-hydroxy-benzoylamino)-azepan-4-yl ester hydrochloride (1:1) from (3R,4R)-3-(4-Hydroxy-benzoylamino)-4-(naphthalene-1-carbonyloxy)-[4-(2-hydroxy-phenoxysulfonyl)-benzoyloxy]-azepane-1-carboxylic acid tert-butyl ester

MS: 527.3 (M+H)$^+$

IR: 3406, 2941, 1724, 1630, 1607, 1545, 1507, 1300, 1277, 1191, 1085, 884, 810, 764 cm$^{-1}$

EXAMPLE II

1) Pd/C 10% was prehydrogenated in a mixture of methanol (5 ml) and tetrahydrofuran, then (3R,4R)-4-(4-Benzyloxy-benzoyloxy)-3-[4-(2,6-bis-benzyloxy-benzoyloxy)-benzoylamino]-azepane-1-carboxylic acid tert-butyl ester was added. The reaction mixture was hydrogenated at room temperature and atmospheric pressure until hydrogen uptake stopped. The catalyst was removed by filtration and the filtrate was evaporated to dryness. The crude product was dissolved in dichloromethane (8 ml), trifluoroacetic acid (4 ml) was added at 0° C. and the reaction mixture was stirred for 1 hour. After removal of the solvent the residue was precipitated with diethylether, filtered and dried in high vacuo to yield 496 mg of pure 4-Hydroxy-benzoic acid (3R,4R)-3-[4-(2,6 -dihydroxy-benzoyloxy)-benzoylamino]-azepan-4-yl ester trifluoroacetate (1:1) (yield 91.6%)

MS: 507 (M+H)$^+$

IR: 3478, 3244, 3073, 1679, 1607, 1543, 1498 cm$^{-1}$

In analogy there was obtained 2) 4-(2,6-Dihydroxy-benzoylamino)-benzoic acid (3R,4R)-3-(4-hydroxy-benzoylamino)-azepan-4-yl ester trifluoroacetate (1:1) from (3R,4R)-4-[4-(2,6-Bis-benzyloxy-benzoylamino)-benzoyloxy]-3-(4-hydroxy-benzoylamino)-azepane-1-carboxylic acid tert-butyl ester

MS: 506.1 (M+H)$^+$

IR: 3310, 3066, 2851, 1677, 1698, 1589, 1544, 1504, 1454 cm$^{-1}$

EXAMPLE III 1) 108.9 g (3R,4R)-3-[4-(Tetrahydro-pyran-2-yloxy)-benzoylamino]-4-[4-(tetrahydro-pyran-2-yloxy)- benzoyloxy]-azepane-1-carboxylic acid tert-butyl ester (mixture of 4 diast.) was dissolved in 200 ml of a 2N dimethoxyethane and i-Pr-OH (1:1) HCl solution at 0° C. The solution was kept at room temperature for 24 h. The deprotected azepine crystallized, and the reaction mixture was cooled to 0° C. before filtration. The white crystals were washed with dry ether then dissolved in pure water. The water solution was extracted twice with ether before being yand lyophilised. 66.4 g (95% yield) 4-Hydroxy-benzoic acid (3R,4R)-3-(4-hydroxy-benzoylamino)-azepan-4-yl ester hydrochloride (1:1) was obtained as a white powder

MS: 371.4 (M+H)$^+$

IR (KBr): 3212, 1702, 1608, 1543, 1508, 1441 cm$^{-1}$

In analogy there were obtained 2) 4-Hydroxy-benzoic acid (3R,4R)-3-[4-(4-hydroxy-benzoyloxy)-benzoylamino]-azepan-4-yl ester hydrochloride (1:1) from (3R,4R) 4-[4-(Tetrahydro-pyran-2-yloxy)-benzoyloxy]-3-{4-(4-(tetrahydro-pyran-2-yloxy)-benzoyloxy]-benzoylamino}-azepane-1-carboxylic acid tert-butyl ester

MS: 491 (M+H)$^+$

IR: 3414, 3239, 3118, 2803, 1706, 1646, 1607, 1562, 1513 cm$^{-1}$ 3) 4-(4-Nitro-benzoyloxy)-benzoic acid (3R,4R)-3-[4-hydroxy-benzoylamino)-azepan-4-yl ester from (3R,4R)-3-[4-(tert-Butyl-dimethyl-silanyloxy)-benzoylamino]-4-[4-(4-nitro-benzoyloxy)-benzoyloxy]-azepane-1-carboxylic acid tert-butyl ester

MS: 520.7 (M+H)$^+$

IR (KBr): 3423, 2955, 2855, 2802, 1745, 1718, 1637, 1606, 1528, 1504 cm$^{-1}$

EXAMPLE IV

The starting compounds used in Examples I–III were prepared by desilylation (A.) and/or hydrogenolytic debenzylation (B.) of corresponding precursors as follows:

A. 754 mg of (3R,4R)-4-(Biphenyl-4-ylcarbonyloxy)-3-[4-(tert-butyl-dimethyl-silanyloxy)-benzoylamino]-azepane-1-carboxylic acid tert-butyl ester were dissolved in 10 ml tetrahydrofuran and 147 mg of tetrabutylammonium-fluoride trihydrate were added at 0° C. and the reaction mixture was stirred for two hours at room temperature. 2.5 ml of a saturated solution of sodium chloride and 2.5 ml of an aqueous 1 molar solution of citric acid were added. The organic layer was concentrated under vacuo diluted with ethyl acetate then washed with 5 ml of a saturated solution of sodium chloride dried over magnesium sulfate and evaporated. The crude compound was purified on silica gel (dichloromethane:ethylacetate 1:1) to yield 551 mg (89% yield) of (3R,4R)-4-(Biphenyl-4-ylcarbonyloxy)-3-(4-hydroxy-benzoylamino)-azepane-1-carboxylic acid tert-butyl ester.

MS: 531 (M+H)$^+$

IR: 3352, 2967, 2933, 1713, 1666, 1609, 1540, 1505, 1417 cm$^{-1}$

B. 80 mg (3R,4R)-4-(4-Benzyloxy-benzoyloxy)-3-[4-(4-fluoro-benzoyloxy)-benzoylamino]-azepane-1-carboxylic acid tert-butyl ester was dissolved in tetrahydrofuran. 10 mg 5% palladium on charcoal was added and the mixture hydrogenated at atmospheric pressure and room temperature for 2 hours. The catalyst was filtered on, the pad washed with tetrahydrofuran and the filtrate evaporated under reduced pressure. The residue was purified by chromatography on silica gel (10 g, AcOEt/Hexane 1:1 eluent) to afford 56 mg (80% yield) (3R,4R)-3-[4-(4-Fluoro-benzoyloxy)-benzoylamino]-4-(4-hydroxy-benzoyloxy)-azepane-1-carboxylic acid tert-butyl ester as a colorless foam

MS: 593.6 (M+H)$^+$

IR: 3400, 1742, 1707, 1664, 1606, 1548, cm$^{-1}$

In analogy there were prepared 1) (3R,4R)-3-(4-Hydroxy-benzoylamino)-4-(naphthalen-2-ylcarbonyloxy)-azepane-1-carboxylic acid tert-butyl ester from (3R,4R)-3-[4-(tert-Butyl-dimethyl-silanyloxy)-benzoylamino]-4-(naphthalen-2-ylcarbonyloxy)-azepane-1-carboxylic acid tert-butyl ester 2) (3R,4R)-3-(4-Hydroxy-benzoylamino)-4-(naphthalen-1-ylcarbonyloxy)-azepane-1-carboxylic acid tert-butyl ester from (3R,4R)-3-[4-(tert-Butyl-dimethyl-silanyloxy)-benzoylamino]-4-(naphthalene-1-ylcarbonyloxy)-azepane-1-carboxylic acid tert-butyl ester 3) (3R,4R)-3-(4-Hydroxy-benzoylamino)-4-(2-phenoxy-benzoyloxy)-azepane-1-carboxylic acid tert-butyl ester from (3R,4R)-3-[4-(tert-Butyl-dimethyl-silanyloxy)-benzoylamino]-4-(2-phenoxy-benzoyloxy)-azepane-1-carboxylic acid tert-butyl ester 4) (3R,4R)-4-(4-tert-Butoxycarbonylamino-benzoyloxy)-3-(4-hydroxy-benzoylamino)-azepane-1-carboxylic acid tert-butyl ester from (3R,4R)-4-(4-Butoxycarbonylamino-benzoyloxy)-3-[4-(tert-butyl-dimethyl-silanyloxy)-benzoylamino]-azepane-1-carboxylic acid tert-butyl ester 5) (3R,4R)-3-(4-Hydroxy-benzoylamino)-4-(3-phenoxy-benzoyloxy)-azepane-1-carboxylic acid tert-butyl ester from (3R,4R)-3-[4-(tert-Butyl-dimethyl-silanyloxy)-benzoylamino]-4-(3-phenoxy-benzoyloxy)-azepane-1-carboxylic acid tert-butyl ester 6) (3R,4R)-4-(Biphenyl-2-ylcarbonyloxy)-3-(4-hydroxy-benzoylamino)-azepane-1-carboxylic acid tert-butyl ester from (3R,4R)-4-(Biphenyl-2-ylcarbonyloxy)-3-[4-(tert-butyl-dimethyl-silanyloxy)-benzoylamino]-azepane-1-carboxylic acid tert-butyl ester 7) 3-Methoxy-phthalic acid (3R,4R)-1-[1-tert-butoxycarbonyl-3-(4-hydroxy-benzoylamino)-azepan-4-yl]ester 2-methyl ester from (3R,4R)-3-Methoxy-phthalic acid (3R,4R)-1-{1-tert-butoxycarbonyl-3-[4-(tert-butyl-dimethyl-silanyloxy)-benzoylamino]-azepan-4-yl}ester 2-methyl ester 8) (3R,4R)-4-(3,5-Dimethoxy-naphthalen-2-ylcarbonyloxy)-3-(4-hydroxy-benzoylamino)-azepane-1-carboxylic acid tert-butyl ester from (3R,4R)-3-[4-(tert-Butyl-dimethyl-silanyloxy)-benzoylamino]-4-(3,5-dimethoxy-naphthalen-2-ylcarbonyloxy)-azepane-1-carboxylic acid tert-butyl ester 9) (3R,4R)-4-(3,7-Dimethoxy-naphthalen-2-ylcarbonyloxy)-3-(4-hydroxy-benzoylamino)-azepane-1-carboxylic acid tert-butyl ester from (3R,4R)-3-[4-(tert-Butyl-dimethyl-silanyloxy)-benzoylamino]-4-(3,7-dimethoxy-naphthalen-2-ylcarbonyloxy)-azepane-1-carboxylic acid tert-butyl ester 10) 4-(2,5-Dichloro-3-nitro-benzoyloxy)-3-(4-hydroxy-benzoylamino)-azepane-1-carboxylic acid tert-butyl ester from (3R,4R)-3-[4-(tert-Butyl-dimethyl-silanyloxy)-benzoylamino]-4-(2,5-dichloro-3-nitro-benzoyloxy)-azepane-1-carboxylic acid tert-butyl ester 11) (E)-(3R,4R)-3-(4-Hydroxy-benzoylamino)-4-[3-(4-hydroxy-phenyl)-acryloyloxy]-azepane-1-carboxylic acid tert-butyl ester from (3R,4R)-3-{4-[Dimethyl-(1,1,2-trimethyl-propyl)-silanyloxy]-benzoylamino}-4-(3-{4-[dimethyl-(1,1,2-trimethyl-propyl)-silanyloxy]-phenyl}-acryloyloxy)-azepane-1-carboxylic acid tert-butyl ester 12) (3R,4R)-4-(3',4'-Dimethoxy-biphenyl-4-ylcarbonyloxy)-3-(4-hydroxy-benzoylamino)-azepane-1- carboxylic acid tert-butyl ester from (E)-(3R,4R)-3-[4-(tert-Butyl-dimethyl-silanyloxy)-benzoylamino]-4-(3',4'-dimethoxy-biphenyl-4-ylcarbonyloxy)-azepane-1-carboxylic acid tert-butyl ester 13) (3R,4R)-4-(3,4-Dihydroxy-benzoyloxy)-3-(4-hydroxy-benzoylamino)-azepane-1-carboxylic acid tert-butyl ester from (3R,4R)-4-(3,4-Bis-benzyloxy-benzoyloxy)-3-(4-hydroxy-benzoylamino)-azepane-1-carboxylic acid tert-butyl ester 14) (3R,4R)-4-(2,3-Dihydroxy-benzoyloxy)-3-(4-hydroxy-benzoylamino)-azepane-1-carboxylic acid tert-butyl ester from (3R,4R)-4-(2,3-Bis-benzyloxy-benzoyloxy)-3-(4-hydroxy-benzoylamino)-azepane-1-carboxylic acid tert-butyl ester 15) (3R,4R)-3-(4-Hydroxy-benzoylamino)-4-(7-hydroxy-3-methoxy-naphthalene-2-ylcarbonyloxy)-azepane-1-carboxylic acid tert-butyl ester from (3R,4R)-4-(7-Benzyloxy-3-methoxy-naphthalen-2-yl-carbonyloxy)-3-(4-hydroxy-benzoylamino)-azepane-1-carboxylic acid tert-butyl ester 16) (3R,4R)-4-(2,4-Dihydroxy-benzoyloxy)-3-(4-hydroxy-benzoylamino)-azepane-1-carboxylic acid tert-butyl ester from (3R,4R)-4-(2,4-Bis-benzyloxy-benzoyloxy)-3-(4-hydroxy-benzoylamino)-azepane-1-carboxylic acid tert-butyl ester 17) (3R,4R)-3-(4-Hydroxy-benzoylamino)-4-(5-hydroxy-3-methoxy-naphthalene-2-ylcarbonyloxy)-azepane-1-carboxylic acid tert-butyl ester from (3R,4R)-4-(5-Benzyloxy-3-methoxy-naphthalen-2-ylcarbonyloxy)-3-(4-hydroxy-benzoylamino)-azepane-1-carboxylic acid tert-butyl ester 18) (3R,4R)-3-(4-Hydroxy-benzoylamino)-4-(3-hydroxy-5-methoxy-naphthalene-2-ylcarbonyloxy)-azepane-1-carboxylic acid tert-butyl ester from (3R,4R)-4-(3-Benzyloxy-5-methoxy-naphthalen-2-yl-carbonyloxy)-3-(4-hydroxy-benzoylamino)-azepane-1-carboxylic acid tert-butyl ester 19) (3R,4R)-3-(4-Hydroxy-benzoylamino)-4-(3-hydroxy-7-methoxy-naphthalen-2-ylcarbonyloxy)-azepane-1-carboxylic acid tert-butyl ester from (3R,4R)-4-(3-Benzyloxy-7-methoxy-naphthalen-2-ylcarbonyloxy)-3-(4-hydroxy-benzoylamino)-azepane-1-carboxylic acid tert-butyl ester 20) (3R,4R)-4-(5-Fluoro-2-hydroxy-benzoyloxy)-3-(4-hydroxy-benzoylamino)-azepane-1-carboxylic acid tert-butyl ester from (3R,4R)-4-(2-Benzyloxy-5-fluoro-benzoyloxy)-3-(4-hydroxy-benzoylamino)-azepane-1-carboxylic acid tert-butyl ester 21) (3R,4R)-3-(4-Hydroxy-benzoylamino)-4-(4-hydroxy-3,5-dimethoxy-benzoyloxy)-azepane-1-carboxylic acid tert-butyl ester (3R,4R)-4-(4-Benzyloxy-3,5-dimethoxy-benzoyloxy)-3-(4-hydroxy-benzoylamino)-azepane-1-carboxylic acid tert-butyl ester 22) (3R,4R)-3-(4-Hydroxy-benzoylamino)-4-[4-(2-hydroxy-benzoylamino)-benzoyloxy]-azepane-1-carboxylic acid tert-butyl ester (3R,4R)-4-[4-(2-Benzyloxy-benzoylamino)-benzoyloxy]-3-(4-hydroxy-benzoylamino)-azepane-1-carboxylic acid tert-butyl ester 23) (3R,4R)-3-(4-Hydroxy-benzoylamino)-4-{4-[(2-hydroxy-benzoyl)-methyl-amino]-benzoyloxy}-azepane-1-carboxylic acid tert-butyl ester from (3R,4R)-4-{4-[(2-Benzyloxy-benzoyl)-methyl-amino]-benzoyloxy}-3-(4-hydroxy-benzoylamino)-azepane-1-carboxylic acid tert-butyl ester 24) (3R,4R)-3-(4-Hydroxy-benzoylamino)-4-(2-hydroxy-benzoyloxy)-azepane-1-carboxylic acid tert-butyl ester from (3R,4R)-4-(2-Benzyloxy-benzoyloxy)-3-(4-hydroxy-benzoylamino)-azepane-1-carboxylic acid tert-butyl ester 25) (3R,4R)-3-(4-Hydroxy-benzoylamino)-4-(naphthalene-1-carbonyloxy)-[4-(2-hydroxy-phenoxysulfonyl)-benzoyloxy]-azepane-1-carboxylic acid tert-butyl ester from (3R,4R)-4-[4-(2-Benzyloxy-phenoxysulfonyl)-benzoyloxy]-3-(4-hydroxy-benzoylamino)-azepane-1-carboxylic acid tert-butyl ester 26) (3R,4R)-4-{4-[(2,6-Dihydroxy-benzoyl)-methyl-amino]-benzoyloxy}-3-(4-hydroxy-benzoylamino)-azepane-1-carboxylic acid tert-butyl ester from (3R,4R)-4-{4-[(2,6-Bis-benzyloxy-benzoyl)-methyl-amino]-benzoyloxy}-3-[4-(tert-butyl-dimethyl-silanyloxy)-benzoylamino]-azepane-1-carboxylic acid tert-butyl ester

EXAMPLE V

The starting compounds used in Example IV were prepared by either a) desilylation of a corresponding precursor (see d) below), or b) esterification of (3R,4R)-4-(4-Benzyloxy-benzoyloxy)-3-(4-hydroxy-benzoylamino)-azepane-1-carboxylic acid tert-butyl ester with 2,6-Bis-benzyloxy-benzoic acid or 4-Fluoro-benzoic acid, or c) esterification of (3R,4R)-3-[4-(tert-Butyl-dimethyl-silanyloxy)-benzoylamino]-4-hydroxy-azepane-1-carboxylic acid tert-butyl ester or (3R,4R)-3-{4-[Dimethyl-(1,1,2-trimethyl-propyl)-silanyloxy]-benzoylamino}-4-hydroxy-azepane-1-carboxylic acid tert-butyl ester with acids activated by sulfonyl chloride, carbodiimide and the like or by esterification of a mixture of (3R,4R)-4-hydroxy-3-[4-[(R)- and-[(S)-tetrahydro-pyran-2-yloxy)-benzoylamino]-azepane-1-carboxylic acid tert-butyl ester and (3R,4R)-4-Hydroxy-3-(4-hydroxy-benzoylamino)-azepane-1-carboxylic acid tert-butyl ester with (RS)-4-(Tetrahydro-pyran-2-yloxy)-benzoic acid or by esterification of (3R,4R)-3-[4-(tert-Butyl-dimethyl-silanyloxy)-benzoylamino]-4-(4-hydroxy-benzoyloxy)-ester with p-nitrobenzoic acid.

In this manner, the following compounds were prepared:

1) (3R,4R)-4-(3,4-Bis-benzyloxy-benzoyloxy)-3-(4-hydroxy-benzoylamino)-azepane-1-carboxylic acid tert-butyl ester from (3R,4R)-4-(3,4-Bis-benzyloxy-benzoyloxy)-3-[4-(tert-butyl-dimethyl-silanyloxy)-benzoylamino]-azepane-1-carboxylic acid tert-butyl ester 2) (3R,4R)-4-(2,3-Bis-benzyloxy-benzoyloxy)-3-(4-hydroxy-benzoylamino)-azepane-1-carboxylic acid tert-butyl ester from (3R,4R)-4-(2,3-Bis-benzyloxy-benzoyloxy)-3-[4-(tert-butyl-dimethyl-silanyloxy)-benzoylamino]-azepane-1-carboxylic acid tert-butyl ester 3) (3R,4R)-4-(7-Benzyloxy-3-methoxy-naphthalen-2-naphthalen-2-naphthaleneyl-2-carbonyloxy)-3-(4-hydroxy-benzoylamino)-azepane-1-carboxylic acid tert-butyl ester from (3R,4R)-4-(7-Benzyloxy-3-methoxy-naphthalen-2-ylcarbonyloxy)-3-[4-(tert-butyl-dimethyl-silanyloxy)-benzoylamino]-azepane-1-carboxylic acid tert-butyl ester 4) (3R,4R)-4-(2,4-Bis-benzyloxy-benzoyloxy)-3-(4-hydroxy-benzoylamino)-azepane-1-carboxylic acid tert-butyl ester from 3R,4R)- 4-(2,4-Bis-benzyloxy-benzoyloxy)-3-{4-[dimethyl-(1,1,2-trimethyl-propyl)-silanyloxy]-benzoylamino}-azepane-1-carboxylic acid tert-butyl ester 5) (3R,4R)-4-(5-Benzyloxy-3-methoxy-naphthalen-2-ylcarbonyloxy)-3-(4-hydroxy-benzoylamino)-azepane-1-carboxylic acid tert-butyl ester from (3R,4R)-4-(5-Benzyloxy-3-methoxy-naphthalen-2-ylcarbonyloxy)-3-[4-(tert-butyl-dimethyl-silanyloxy)-benzoylamino]-azepane-1-carboxylic acid tert-butyl ester 6) (3R,4R)-4-(3-Benzyloxy-5-methoxy-naphthalen-2-ylcarbonyloxy)-3-(4-hydroxy-benzoylamino)-azepane-1-carboxylic acid tert-butyl ester from (3R,4R)-4-(3-Benzyloxy-5-methoxy-naphthalen-2-ylcarbonyloxy)-3-[4-(tert-butyl-dimethyl-silanyloxy)-benzoylamino]-azepane-1-carboxylic acid tert-butyl ester 7) (3R,4R)-4-(3-Benzyloxy-7-methoxy-naphthalen-2-ylcarbonyloxy)-3-(4-hydroxy-benzoylamino)-azepane-1-carboxylic acid tert-butyl ester from (3R,4R)-4-(3-Benzyloxy-7-methoxy-naphthalen-2-ylcarbonyloxy)-3-[4-(tert-butyl-dimethyl-silanyloxy)-benzoylamino]-azepane-1-carboxylic acid tert-butyl ester 8) (3R,4R)-4-(2-Benzyloxy-5-fluoro-benzoyloxy)-3-(4-hydroxy-benzoylamino)-azepane-1-carboxylic acid tert-butyl ester from (3R,4R)-4-(2-Benzyloxy-5-fluoro-benzoyloxy)-3-[4-(tert-butyl-dimethyl-silanyloxy)-benzoylamino]-azepane-1-carboxylic acid tert-butyl ester 9) (3R,4R)-4-(4-Benzyloxy-3,5-dimethoxy-benzoyloxy)-3-(4-hydroxy-benzoylamino)-azepane-1-carboxylic acid tert-butyl ester from (3R,4R)-4-(4-Benzyloxy-3,5-dimethoxy-benzoyloxy)-3-{4-[dimethyl-(1,1,2-trimethyl-propyl)-silanyloxy]-benzoylamino}-azepane-1-carboxylic acid tert-butyl ester 10) (3R,4R)-4-[4-(2-Benzyloxy-benzoylamino)-benzoyloxy]-3-(4-hydroxy-benzoylamino)-azepane-1-carboxylic acid tert-butyl ester from (3R,4R)-4-[4-(2-Benzyloxy-benzoylamino)-benzoyloxy]-3-[4-(tert-butyl-dimethyl-silanyloxy)-benzoylamino]-azepane-1-carboxylic acid tert-butyl ester 11) (3R,4R)-4-[4-(2,6-Bis-benzyloxy-benzoylamino)-benzoyloxy]-3-(4-hydroxy-benzoylamino)-azepane-1-carboxylic acid tert-butyl ester from (3R,4R)-4-[4-(2,6-Bis-benzyloxy-benzoylamino)-benzoyloxy]3-[4-tert-butyl-dimethyl-silanyloxy)-benzoylamino]-azepane-1-carboxylic acid tert-butyl ester 12) (3R,4R)-4-{4-[(2-Benzyloxy-benzoyl)-methyl-amino]-benzoyloxy}-3-(4-hydroxy-benzoylamino)-azepane-1-carboxylic acid tert-butyl ester from (3R,4R)-4-{4-[(2-Benzyloxy-benzoyl)-methyl-amino]-benzoyloxy}-3-[4-(tert-butyl-dimethyl-silanyloxy)-benzoylamino]-azepane-1-carboxylic acid tert-butyl ester 13) (3R,4R)-4-(2-Benzyloxy-benzoyloxy)-3-(4-hydroxy-benzoylamino)-azepane-1-carboxylic acid tert-butyl ester from (3R,4R)- 4-(2-Benzyloxy-benzoyloxy)-3-{4-[dimethyl-(1,1,2-trimethyl-propyl)-silanyloxy]-benzoylamino}-azepane-1-carboxylic acid tert-butyl ester 14) (3R,4R)-4-[4-(2-Benzyloxy-phenoxysulfonyl)-benzoyloxy]-3-(4-hydroxy-benzoylamino)-azepane-1-carboxylic acid tert-butyl ester from (3R,4R)-4-[4-(2-Benzyloxy-phenoxysulfonyl)-benzoyloxy]-3-{4-[dimethyl-(1,1,2-trimethyl-propyl)-silanyloxy]-benzoylamino}-azepane-1-carboxylic acid tert-butyl ester 15) (3R,4R)-4-(4-Benzyloxy-benzoyloxy)-3-(4-hydroxy-benzoylamino)-azepane-1-carboxylic acid tert-butyl ester from (3R,4R)-4-(4-Benzyloxy-benzoyloxy)-3-[4-(tert-butyl-dimethyl-silanyloxy)-benzoylamino]-azepane-1-carboxylic acid tert-butyl ester 16) (3R,4R)-4-(4-Benzyloxy-benzoyloxy)-3-(4-(2,6-bis-benzyloxy-benzoyloxy)-benzoylamino]-azepane-1-carboxylic acid tert-butyl ester from (3R,4R)-4-(4-Benzyloxy-benzoyloxy)-3-(4-hydroxy-benzoylamino)-azepane-1-carboxylic acid tert-butyl ester and 2,6-Bis-benzyloxy-benzoic acid 17) (3R,4R)-4-(4-Benzyloxy-benzoyloxy)-3-[4-(4-fluoro-benzoyloxy)-benzoylamino]-azepane-1-carboxylic acid tert-butyl ester from (3R,4R)-4-(4-Benzyloxy-benzoyloxy)-3-(4-hydroxy-benzoylamino)-azepane-1-carboxylic acid tert-butyl ester and 4-Fluoro-benzoic acid 18) (3R,4R)-4-(Biphenyl-4-ylcarbonyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and Biphenyl-4-carboxylic acid 19) (3R,4R)-3-[4-(tert-Butyl-dimethyl-silanyloxy)-benzoylamino]-4-(naphthalen-2-ylcarbonyloxy)-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and Naphthalene-2-carboxylic acid 20) (3R,4R)-3-[4-(tert-Butyl-dimethyl-silanyloxy)-benzoylamino]-4-(naphthalene-1-ylcarbonyloxy)-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and Naphthalene-1-carboxylic acid 21) (3R,4R)-3-[4-(tert-Butyl-dimethyl-silanyloxy)-benzoylamino]-4-(2-phenoxy-benzoyloxy)-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 2-Phenoxy-benzoic acid 22) (3R,4R)-4-(4-tert-Butoxycarbonylamino-benzoyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 4-tert-Butoxycarbonylamino-benzoic acid 23) (3R,4R)-3-[4-(tert-Butyl-dimethyl-silanyloxy)-benzoylamino]-4-(3-phenoxy-benzoyloxy)-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 4-Phenoxy-benzoic acid 24) (3R,4R)-4-(Biphenyl-2-ylcarbonyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and Biphenyl-2-carboxylic acid 25) (3R,4R)-3-Methoxy-phthalic acid (3R,4R)-1-{1-tert-butoxycarbonyl-3-[4-(tert-butyl-dimethyl-silanyloxy)-benzoylamino]-azepan-4-yl}ester 2-methyl ester from (3R,4R)-3-[4-(tert-Butyl-dimethyl-silanyloxy)-benzoylamino]-4-hydroxy-azepane-1-carboxylic acid tert-butyl ester and 3-Methoxy-phthalic acid 2-methyl ester 26) (3R,4R)-3-[4-(tert-Butyl-dimethyl-silanyloxy)-benzoylamino]-4-(3,5-dimethoxy-naphthalen-2-ylcarbonyloxy)-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 3,5-Dimethoxy-naphthalene-2-carboxylic acid 27) (3R,4R)-3-[4-(tert-Butyl-dimethyl-silanyloxy)-benzoylamino]-4-(3,7-dimethoxy-naphthalen-2-ylcarbonyloxy)-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 3,7-Dimethoxy-naphthalene-2-carboxylic acid 28) (3R,4R)-3-[4-(tert-Butyl-dimethyl-silanyloxy)-benzoylamino]-4-(2,5-dichloro-3-nitro-benzoyloxy)-azepane-1-carboxylic acid tert-butyl ester from (3R,4R)-3-[4-(tert-Butyl-dimethyl-silanyloxy)-benzoylamino]-4- hydroxy-azepane-1-carboxylic acid tert-butyl ester and 2,5-Dichloro-3-nitro-benzoic acid
29) (3R,4R)-3-{4-(Dimethyl-(1,1,2-trimethyl-propyl)-silanyloxy]-benzoylamino}-4-(3-{4-(dimethyl-(1,1,2-trimethyl-propyl)-silanyloxy]-phenyl}-acryloyloxy)-azepane-1-carboxylic acid tert-butyl ester from (3R,4R)-3-{4-[Dimethyl-(1,1,2-trimethyl-propyl)-silanyloxy]-benzoylamino}-4-hydroxy-azepane-1-carboxylic acid tert-butyl ester and (E)-(3R,4R)-3-{4-[Dimethyl-(1,1,2-trimethyl-propyl)-silanyloxy]-phenyl}-acrylic acid
30) (E)-(3R,4R)-3-[4-(tert-Butyl-dimethyl-silanyloxy)-benzoylamino]-4-(3',4'-dimethoxy-biphenyl-4-ylcarbonyloxy)-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 3',4'-Dimethoxy-biphenyl-4-carboxylic acid
31) (3R,4R)-4-(3,4-Bis-benzyloxy-benzoyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 3,4-Bis-benzyloxy-benzoic acid
32) (3R,4R)-4-(2,3-Bis-benzyloxy-benzoyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 2,3-Bis-benzyloxy-benzoic acid
33) (3R,4R)-4-(7-Benzyloxy-3-methoxy-naphthalen-2-ylcarbonyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 7-Benzyloxy-3-methoxy-naphthalene-2-carboxylic acid
34) (3R,4R)-4-(2,4-Bis-benzyloxy-benzoyloxy)-3-{4-[dimethyl-(1,1,2-trimethyl-propyl)-silanyloxy]-benzoylamino}-azepane-1-carboxylic acid tert-butyl ester from (3R,4R)-3-{4-[Dimethyl-(1,1,2-trimethyl-propyl)-silanyloxy]-benzoylamino}-4-hydroxy-azepane-1-carboxylic acid tert-butyl ester and 2,4-Bis-benzyloxy-benzoic acid
35) (3R,4R)-4-(5-Benzyloxy-3-methoxy-naphthalen-2-ylcarbonyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 5-Benzyloxy-3-methoxy-naphthalene-2-carboxylic acid
36) (3R,4R)-4-(3-Benzyloxy-5-methoxy-naphthalen-2-ylcarbonyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 3-Benzyloxy-5-methoxy-naphthalene-2-carboxylic acid
37) (3R,4R)-4-(3-Benzyloxy-7-metahoxy-naphthalen-2-ylcarbonyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 3-Benzyloxy-7-methoxy-naphthalene-2-carboxylic acid
38) (3R,4R)-4-(2-Benzyloxy-5-fluoro-benzoyloxy)-3-[4-(tert-butyl-dimethyl-silanyloxy)-benzoylamino]-azepane-1-carboxylic acid tert-butyl ester from (3R,4R)-3-[4-(tert Butyl-dimethyl-silanyloxy)-benzoylamino]-4-hydroxy-azepane-1-carboxylic acid tert-butyl ester and 2-Benzyloxy-5-fluoro-benzoic acid
39) (3R,4R)-4-(4-Benzyloxy-3,5-dimethoxy-benzoyloxy)-3-{4-[dimethyl-(1,1,2-trimethyl-propyl)-silanyloxy]-benzoylamino}-azepane-1-carboxylic acid tert-butyl ester from (3R,4R)-3-{4-[Dimethyl-(1,1,2-trimethyl-propyl)-silanyloxy]-benzoylamino}-4-hydroxy-azepane-1-carboxylic acid tert-butyl ester and 4-Benzyloxy-3,5-dimethoxy-benzoic acid
40) (3R,4R)-4-[4-(2-Benzyloxy-benzoylamino)-benzoyloxy]-3-[4-tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 4-(2-Benzyloxy-benzoylamino)-benzoic acid
41) (3R,4R)-4-[4-(2,6-Bis-benzyloxy-benzoylamino)-benzoyloxy]-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 4-(2,6-Bis-benzyloxy-benzoylamino)-benzoic acid
42) (3R,4R)-4-{4-[(2-Benzyloxy-benzoyl)-methyl-amino]-benzoyloxy}-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 4-[(2-Benzyloxy-benzoyl)-methyl-amino]-benzoic acid
43) (3R,4R)-4-{4-[(2,6-Bis-benzyloxy-benzoyl)-methyl-amino]-benzoyloxy}-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 4-[(2,6-Bis-benzyloxy-benzoyl)-methyl-amino]-benzoic acid
44) (3R,4R)-4-(2-Benzyloxy-benzoyloxy)-3-{4-(dimethyl-(1,1,2-trimethyl-propyl)-silanyloxy]-benzoylamino}-azepane-1-carboxylic acid tert-butyl ester from (3R,4R)-3-{4-[Dimethyl-(1,1,2-trimethyl-propyl)-silanyloxy]-benzoylamino}-4-hydroxy-azepane-1-carboxylic acid tert-butyl ester and 2-Benzyloxy-benzoic acid
45) (3R,4R)-4-[4-(2-Benzyloxy-phenoxysulfonyl)-benzoyloxy]-3-{4-[dimethyl-(1,1,2-trimethyl-propyl)-silanyloxy]-benzoylamino}-azepane-1-carboxylic acid tert-butyl ester from (3R,4R)-3-{4-[Dimethyl-(1,1,2-trimethyl-propyl)-silanyloxy]-benzoylamino}-4-hydroxy-azepane-1-carboxylic acid tert-butyl ester and 4-(2-Benzyloxy-phenoxysulfonyl)-benzoic acid
46) (3R,4R)-4-(4-Benzyloxy-benzoyloxy)-3-[4-(tert-butyl-dimethyl-silanyloxy)-benzoylamino]-azepane-1-carboxylic acid tert-butyl ester from (3R,4R)-3-[4-(tert-Butyl-dimethyl-silanyloxy)-benzoylamino]-4-hydroxy-azepane-1-carboxylic acid tert-butyl ester and 4-Benzyloxy-benzoic acid
47) (3R,4R)-3-[4-(Tetrahydro-pyran-2-yloxy)-benzoylamino]-4-[4-(tetrahydro-pyran-2-yloxy)-benzoyloxy]-azepane-1-carboxylic acid tert-butyl ester (mixture of 4 diast.) from mixture of (3R,4R)-4-hydroxy-3-[4-[(R)- and-[(S)-tetrahydro-pyran-2-yloxy)-benzoylamino]-azepane-1-carboxylic acid tert-butyl ester and (RS)-4-(Tetrahydro-pyran-2-yloxy)-benzoic acid
48) (3R,4R) 4-[4-(Tetrahydro-pyran-2-yloxy)-benzoyloxy]-3-{4-[4-(tetrahydro-pyran-2-yloxy)-benzoyloxy]-benzoylamino}-azepane-1-carboxylic acid tert-butyl ester from (3R,4R)-4-Hydroxy-3-(4-hydroxy-benzoylamino)-azepane-1-carboxylic acid tert-butyl ester and (RS)-4-(Tetrahydro-pyran-2-yloxy)-benzoic acid 49) (3R,4R)-3-[4-(tert-Butyl-dimethyl-silanyloxy)-benzoylamino]-4-[4-(4-nitro-benzoyloxy)-benzoyloxy]-azepane-1-carboxylic acid tert-butyl ester from (3R,4R)-3-[4-(tert-Butyl-dimethyl-silanyloxy)-benzoylamino]-4-(4-hydroxy-benzoyloxy)-azepane-1-carboxylic acid tert-butyl ester and 4-Nitro-benzoic acid 50) (3R,4R)-3,4-Dihydroxy-azepane-1-carboxylic acid tert-butyl ester was prepared by hydrogenation of (3R,4R)-4-Benzyloxy-3-hydroxy-azepane-1-carboxylic acid tert-butyl ester

EXAMPLE VI

Examples of esters and their preparation used in Example V d) are 1) mixture of (3R,4R)-4-hydroxy-3-[4-[(R)- and -[(S)-tetrahydro-pyran-2-yloxy)-benzoylamino]-azepane-1-carboxylic acid tert-butyl ester by hydrogenation of mixture of (3R,4R)-4-benzyloxy-3-[4-[(R)- and -[(S)-tetrahydro-pyran-2-yloxy)-benzoylamino]-azepane-1-carboxylic acid tert-butyl ester which is prepared by esterification of (3R,4R)-3-Amino-4-benzyloxy-azepane-1-carboxylic acid tert-butyl ester and (RS)-4-(Tetrahydro-pyran-2-yloxy)-benzoic acid 2) (3R,4R)-4-Hydroxy-3-(4-hydroxy-benzoylamino)-azepane-1-carboxylic acid tert-butyl ester by hydrogenation of (3R,4R)-4-Benzyloxy-3-(4-benzyloxy-benzoylamino)-azepane-1-carboxylic acid tert-butyl ester which is prepared by esterification of (3R,4R)-3-Amino-4-benzyloxy-azepane-1-carboxylic acid tert-butyl ester and 4-benzyloxy-benzoic acid 3) (3R,4R)-3-[4-(tert-Butyl-dimethyl-silanyloxy)-benzoylamino]-4-(4-hydroxy-benzoyloxy)-azepane-1-carboxylic acid tert-butyl ester by hydrogenation of (3R,4R)-4-(4-Benzyloxy-benzoyloxy)-3-[4-(tert-butyl-dimethyl-silanyloxy)-benzoylamino]-azepane-1-carboxylic acid tert-butyl ester

EXAMPLE VII

Preparation of tert-Butyl (3R,4R)-3-amino-4-benzyloxy-azepane-1-carboxylate:

Ethyl 2,3-dideoxy-alpha-D-erythrohexopyranoside was converted with p-toluenesulphonyl chloride into ethyl 6O-(p-tolylsulphonyl)-2,3-dideoxy-alpha-D-erythrohexopyranoside. By reaction with sodium azide, there was obtained therefrom ethyl 6-azido-2,3,6-trideoxy-a-D-erythrohexopyranoside and therefrom with 4-nitrobenzoic acid under Mitsunobu conditions there was obtained ethyl 6-azido-2,3,6-trideoxy-4-O(4-nitrobenzoyl)-alpha-D-threohexopyranoside. Basic hydrolysis of the latter compound yielded ethyl 6-azido-2,3,6-trideoxy-a-D-galactopyranoside which by benzylation and subsequent acidic hydrolysis was converted into 6-azido-5O-benzyl-2,3,6-trideoxy-D-galactopyranose. Catalytic hydrogenation (PtO/room temperature) and subsequent reaction with bis-tert-butyl carbonate yielded tert butyl (3S,4R)-4-(benzyloxy)-hexahydro-3-hydroxy-1H-azepine-1-carboxylate. Acylation under Mitsunobu conditions to tert butyl (3S,4R)-4-(benzyloxy)-hexahydro-3-O-(4-nitrobenzoyl)-1H-azepine-1-carboxylate, basic hydrolysis and reaction with hydrazoic acid under Mitsunobu conditions yielded tert-butyl (3R,4R)-3-azido-4-(benzyloxy)-hexahydro-1H-azepine-1-carboxylate, from which tert-Butyl (3R,4R)-3-amino-4-benzyloxy-azepane-1-carboxylate was obtained by hydrogenation (Pd/C).

EXAMPLE VIII

Other starting materials used in the preceding Examples were obtained as follows:

1) 7-Benzyloxy-3-methoxy-naphthalene-2-carboxylic acid from 3,7-Dihydroxy-naphthalene-2-carboxylic acid via 7-Benzyloxy-3-hydroxy-naphthalene-2-carboxylic acid methyl ester and 7-Benzyloxy-3-methoxy-naphthalene-2-carboxylic acid methyl ester;

2) 5-Benzyloxy-3-methoxy-naphthalene-2-carboxylic acid from 3,5-Dihydroxy-naphthalene-2-carboxylic acid via 5-Benzyloxy-3-hydroxy-naphthalene-2-carboxylic acid methyl ester; and 5-Benzyloxy-3-methoxy-naphthalene-2-carboxylic acid methyl ester;

3) 3-Benzyloxy-5-methoxy-naphthalene-2-carboxylic acid from 3-Hydroxy-5-methoxy-naphthalene-2-carboxylic acid methyl ester via 3-Benzyloxy-5-methoxy-naphthalene-2-carboxylic acid methyl ester;

4) 3-Benzyloxy-7-methoxy-naphthalene-2-carboxylic acid from 3-Hydroxy-7-methoxy-naphthalene-2-carboxylic acid methyl ester via 3-Benzyloxy-7-methoxy-naphthalene-2-carboxylic acid methyl ester;

5) 4-(2,6-Bis-benzyloxy-benzoylamino)-benzoic acid from 2,6-Bis-benzyloxy-benzoic acid and 4-Amino-benzoic acid methyl ester via 4-(2,6-Bis-benzyloxy-benzoylamino)-benzoic acid methyl ester;

6) 4-[(2-Benzyloxy-benzoyl)-methyl-amino]-benzoic acid from 4-(2-Benzyloxy-benzoylamino)-benzoic acid methyl ester via 4-[(2-Benzyloxy-benzoyl)-methyl-amino]-benzoic acid methyl ester;

7) 4-[(2,6-Bis-benzyloxy-benzoyl)-methyl-amino]-benzoic acid from 4-(2,6-Bis-benzyloxy-benzoylamino)-benzoic acid methyl ester via 4-[(2,6-Bis-benzyloxy-benzoyl)-methyl-amino]-benzoic acid methyl ester;

8) (E)-(3R,4R)-3-{4-[Dimethyl-(1,1,2-trimethyl-propyl)-silanyloxy]-phenyl}-acrylic acid from (E)-3-(4-Hydroxy-phenyl)-acrylic acid;

9) 4-(2-Benzyloxy-phenoxysulfonyl)-benzoic acid from 2-Benzyloxy-phenol and 4-Chlorosulfonyl-benzoic acid.

Examples A–F illustrate the manufacture of pharmaceutical preparations.

EXAMPLE A

Hard gelatin capsules can be produced as follows:

| Ingredients | mg/capsule |
|---|---|
| 1. Spray-dried powder containing 75% compound I | 20 |
| 2. Sodium dioctylsulphocuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 120.0 |

The spray-dried powder, which is based on the active ingredient, gelatin and microcrystalline cellulose and which has an average active ingredient particle size of <1μ (measured by autocorrelation spectroscopy), is moistened with an aqueous solution of sodium carboxymethylcellulose and sodium dioctylsulphocuccinate and kneaded. The resulting mass is granulated dried and sieved. The granulate obtained is mixed with microcrystalline cellulose, talc and magnesium stearate. The mixture is filled into size 0 capsules.

EXAMPLE B

Tablets can be produced as follows:

| Ingredients | mg/tablet |
| --- | --- |
| 1. Compound I as a finely milled powder | 20 |
| 2. Powd. lactose | 100 |
| 3. White corn starch | 60 |
| 4. Povidone K30 | 8 |
| 5. White corn starch | 112 |
| 6. Talc | 16 |
| 7. Magnesium stearate | 4 |
| Total | 320 |

The finely milled substance is mixed with lactose and the (3.) portion of the corn starch. The mixture is moistened with an aqueous solution of Povidone K30 and kneaded, and the resulting mass is granulated, dried and sieved. The granulate is mixed with the remaining corn starch (5.), talc and magnesium stearate and pressed to tablets of suitable size.

EXAMPLE C

Soft gelatin capsules can be produced as follows:

| Ingredients | mg/capsule |
| --- | --- |
| 1. Compound I | 5 |
| 2. Triglyceride | 450 |
| Total | 455 |

10 g of compound I are dissolved in 90 g of medium chain triglyceride with stirring, inert gasification and protection from light. This solution is processed as a capsule fill mass to soft gelatin capsules containing 5 mg of active ingredient.

EXAMPLE D

A cream can be produced from the ingredients listed hereinafter in a known manner:

| | Wt. % |
| --- | --- |
| Compound of Formula I. | 0.1–5 |
| Cetyl alcohol | 5.25–8.85 |
| Arlacel 165 (glyceryl/PEG 100 stearate) | 3.75–6.25 |
| Miglyol 818 (caprylic/capric/linoleic acid) | 11.25–18.75 |
| Sorbitol solution | 3.75–6.25 |
| EDTA Na$_2$ | 0.075–0.125 |
| Carbopol 934P (carbomer 934P) | 0.15–0.25 |
| Butylated hydroxyanisole | 0.0375–0.0625 |
| Methylparaben | 0.135–0.225 |
| Propylparaben | 0.0375–0.0625 |
| NaOH (10% solution) | 0.15–0.25 |
| Water q.s. | 100.00 |

The physical properties of the preparations can be altered by varying the ratio between the adjuvants.

EXAMPLE E

A gel can be produced from the ingredients listed hereinafter in a known manner:

| | Wt. % |
| --- | --- |
| Compound of Formula I | 0.1–5 |
| Pluronic L 101 (poloxamer 331) | 10.00 |
| Aerosil (silicion dioxide) | 8.00 |
| PCL liquid (fatty acid ester) | 15.00 |
| Cetiol V (decyl oleate) | 20.00 |
| Neobee oil (medium chain length triglyceride) | 15.00 |
| Euhanol G (octyldodecanol), q.s. | 100.00 |

EXAMPLE F

A solution can be prepared from the following ingredients

| Ingredients | mg |
| --- | --- |
| Compound of formula I | 10 |
| Propylene glycol | 100 |
| Ethanol 94% (V/V) | 300 |
| Phosphoric acid ca. 85% | 5 |
| 1 N NaOH ad pH 3 | |
| Demineralized water ad 1 ml | |

What is claimed is:

1. The compound which is
   4-Hydroxy-benzoic acid (3R,4R)-3-[4-(4-fluoro-benzoyloxy)-benzoylamino]-azepan-4-yl ester.
2. The compound which is
   4-Hydroxy-benzoic acid (3R,4R)-3-[4-(2,6-dihydroxy-benzoyloxy)-benzoylamino]-azepan-4-yl ester.
3. The compound which is
   4-Hydroxy-benzoic acid (3R,4R)-3-[4-(4-hydroxy-benzoyloxy)-benzoylamino]-azepan-4-yl ester.
4. The compound which is
   3-Methoxy-phthalic acid (3R,4R)-1-[3-(4-hydroxy-benzoylamino)-azepan-4-yl]ester 2-methyl ester.
5. The compound which is
   2,5-Dichloro-3-nitro-benzoic acid (3R,4R)-3-(4-hydroxy-benzoylamino)-azepan-4-yl ester.
6. The compound which is
   3-(4-Hydroxy-phenyl)-acrylic acid (3R,4R)-3-(4-hydroxy-benzoylamino)-azepan-4-yl ester.
7. The compound which is
   3',4'-Dimethoxy-biphenyl-4-carboxylic acid (3R,4R)-3-(4-hydroxy-benzoylamino)-azepan-4-yl ester.
8. The compound which is
   4-[(2-Hydroxy-benzoyl)-methyl-amino]-benzoic acid (3R,4R)-3-(4-hydroxy-benzoylamino)-azepan-4-yl ester.
9. The compound which is
   4-[(2,6-Dihydroxy-benzoyl)-methyl-amino]-benzoic acid (3R,4R)-3-(4-hydroxy-benzoylamino)-azepan-4-yl ester.
10. The compound which is
    4-(2-Hydroxy-phenoxysulfonyl)-benzoic acid (3R,4R)-3-(4-hydroxy-benzoylamino)-azepan-4-yl ester.
11. The compound which is
    4-(4-Nitro-benzoyloxy)-benzoic acid (3R,4R)-3-(4-hydroxy-benzoylamino)-azepan-4-yl ester.

* * * * *